United States Patent
Yaffe et al.

(10) Patent No.: US 11,697,026 B2
(45) Date of Patent: Jul. 11, 2023

(54) SYSTEMS AND METHODS CONFIGURED TO DEPLOY CUFFS ONTO BIOLOGICAL STRUCTURES

(71) Applicant: Galvani Bioelectronics Limited, Brentford (GB)

(72) Inventors: Benjamin Yaffe, Research Triangle Park, NC (US); Kenneth Douglas Rys, Research Triangle Park, NC (US)

(73) Assignee: GALVANI BIOELECTRONICS LIMITED, Brentford (GB)

( * ) Notice: Subject to any disclaimer, the term of this patent is extended or adjusted under 35 U.S.C. 154(b) by 87 days.

(21) Appl. No.: 15/733,239

(22) PCT Filed: Dec. 14, 2018

(86) PCT No.: PCT/US2018/065640
§ 371 (c)(1),
(2) Date: Jun. 15, 2020

(87) PCT Pub. No.: WO2019/118824
PCT Pub. Date: Jun. 20, 2019

(65) Prior Publication Data
US 2021/0093853 A1    Apr. 1, 2021

Related U.S. Application Data

(60) Provisional application No. 62/599,261, filed on Dec. 15, 2017.

(51) Int. Cl.
*A61N 1/05* (2006.01)
*A61N 1/372* (2006.01)
*A61B 17/34* (2006.01)

(52) U.S. Cl.
CPC .......... *A61N 1/372* (2013.01); *A61B 17/3468* (2013.01); *A61N 1/0558* (2013.01); *A61N 1/37205* (2013.01); *A61N 1/0556* (2013.01)

(58) Field of Classification Search
CPC .... A61N 1/0556; A61N 1/0558; A61N 1/372; A61N 1/37205; A61B 17/3468
See application file for complete search history.

(56) References Cited

U.S. PATENT DOCUMENTS 4,881,939 A    11/1989  Arnold
5,951,587 A *   9/1999  Qureshi ............... A61B 17/062
                                                  606/147

(Continued)

FOREIGN PATENT DOCUMENTS

WO    WO 2013/159136        10/2013
WO    WO 2013/159136 A1     10/2013

(Continued)

OTHER PUBLICATIONS

International Search Report and Written Opinion, Application No. PCT/US18/65640, dated May 28, 2019, 10 pages.

(Continued)

*Primary Examiner* — Pamela M. Bays
(74) *Attorney, Agent, or Firm* — Merchant & Gould P.C.

(57) ABSTRACT

An implant insertion system and methods of use of the implant insertion system are disclosed. The implant insertion system includes an implant and an instrument configured to deliver the implant to a biological structure and assist in deploying the implant to the biological structure. The instrument includes a retention member the secures the implant to the instrument and retains the implant in a first configuration. The retention member is movable to decouple the implant from the instrument. The implant is configured to transition from the first configuration to a second configuration, such that in the second configuration the implant is secured to the biological structure.

19 Claims, 10 Drawing Sheets

(56) References Cited

U.S. PATENT DOCUMENTS

| | | | |
|---|---|---|---|
| 5,964,702 A | 10/1999 | Grill | |
| 9,113,861 B2 | 8/2015 | Martin | |
| 2003/0109914 A1* | 6/2003 | Westlund | A61N 1/056 607/122 |
| 2006/0136024 A1 | 6/2006 | Cohen et al. | |
| 2008/0196939 A1* | 8/2008 | Lubenow | A61N 1/057 174/652 |
| 2009/0069803 A1 | 3/2009 | Starkebaum | |
| 2009/0210042 A1 | 8/2009 | Czewski | |
| 2010/0298920 A1 | 11/2010 | Mrva | |
| 2014/0214135 A1 | 7/2014 | Ben-David et al. | |
| 2014/0228905 A1 | 8/2014 | Bolea | |
| 2015/0202433 A1 | 7/2015 | Franke et al. | |
| 2016/0345963 A1 | 12/2016 | Langley | |

FOREIGN PATENT DOCUMENTS

| | | |
|---|---|---|
| WO | WO 2019020985 A1 | 1/2019 |
| WO | WO 2019133515 A | 7/2019 |

OTHER PUBLICATIONS

International Report on Patentability and Written Opinion, International Application No. PCT/GB2018/053597, dated Jun. 16, 2020, 9 pages.

International Search Report and Written Opinion, International Application No. PCT/US2018/065640, dated May 28, 2019, 11 pages.

European Search Report, European Application No. 18889316.8, dated Jul. 29, 2021, 8 pages.

\* cited by examiner

SYSTEMS AND METHODS CONFIGURED TO DEPLOY CUFFS ONTO BIOLOGICAL STRUCTURES

PRIORITY CLAIM

The present application is a National Phase entry of PCT Application No. PCT/US2018/065640, filed Dec. 14, 2018, which claims priority from U.S. Provisional Application No. 62/599,261 filed Dec. 15, 2017, each of which is hereby fully incorporated herein by reference.

TECHNICAL FIELD

The present disclosure is related to embodiments of an implant, embodiments of an instrument configured to insert the implant, and methods of inserting the implant using the instrument. More specifically, the present disclosure is directed to embodiments of a cuff configured to be secured to a biological structure, instruments configured to insert the cuff, and methods of inserting the cuff.

BACKGROUND

Implants can be used to deliver therapy to various biological structures of a patient. A cuff is a type of implant used to deliver therapy to soft tissues. A cuff can be configured to be secured to a soft tissue and separate the soft tissue from surrounding biological structures. A cuff can be configured to deliver electrical stimulation to the soft tissue.

U.S. Pat. No. 4,881,939 discloses an implantable helical cuff that defines coils, which turn about a central axis. The implantable helical cuff is wound about an artery much like a telephone cord may be wound around a pencil.

U.S. Pub. No. 2009/0210042 discloses an implantable circumferentially adjustable cuff, and a method of attaching the cuff to an internal body tissue including the steps of wrapping the cuff around the body tissue and fastening a tail end portion of the cuff with a head end portion of the cuff.

U.S. Pub. No. 2010/0298920 discloses a cuff electrode and an applicator tool. The applicator tool includes an open ended, inverted trough, which the cuff electrode mounts to in an uncoiled configuration. The applicator tool further includes a slider, which pushes the cuff electrode off the trough, allowing the cuff electrode to coil around a nerve positioned within the open ended, inverted trough.

Each of the above examples illustrate a variety of existing implantable cuffs and instruments configured to deploy the cuffs to a biological structure. However, these examples also illustrate deployment of implantable cuffs in shapes that may make the approach to the biological structure difficult, and may include complex movements of either the cuff, the insertion instrument, or both, to deploy and secure the cuff to the biological structure. A cuff and insertion instrument configured to deliver the cuff to a biological structure in a shape with a minimal profile and to deploy the cuff onto the biological structure using simple movements may result in a more efficient procedure that requires less space within the patient's body, and smaller openings in patients receiving the cuff.

SUMMARY

According to an aspect of the disclosure, an implant insertion instrument includes a body member including a distal surface and a proximal surface, the distal surface spaced from the proximal surface in a first direction such that the distal surface faces the proximal surface, the body member further including a first side surface and a second side surface, the first side surface spaced from the second side surface in a second direction, which is perpendicular to the first direction, such that the first side surface faces the second side surface, the body member further including a base surface that extends between the distal surface and the proximal surface in the first direction, and further extends between the first side surface and the second side surface in the second direction.

The implant insertion instrument including a pocket defined by the body member such that the pocket extends from the proximal surface to the distal surface in the first direction, further extends from the second side surface to the first side surface in the second direction, and further extends into the body member in a third direction, which is perpendicular to both the first direction and the second direction, to the base surface. The implant insertion instrument further including a retention member configured to be movably attached to body member such that the retention member is movable from a first position relative to body member to a second position relative to the body member, in the first position a portion of the retention member is aligned with a portion of the base surface in the third direction, and in the second position the portion of the retention member is offset from the portion of the base surface in the third direction.

According to an aspect of the disclosure, an implant insertion instrument includes a body member including a base surface and an outer surface, the outer surface opposite the base surface with respect to a first direction. The implant insertion instrument further including a first recess and a second recess. The first recess defined by the body member, the first recess extending into the base surface toward the outer surface and terminating between the base surface and the outer surface with respect to the first direction. The second recess defined by the body member, the second recess extending into the base surface toward the outer surface and terminating between the base surface and the outer surface with respect to the first direction, the first recess spaced from the second recess in a second direction, which is perpendicular to the first direction.

The implant insertion instrument including an aperture defined by the body member, the aperture extending in the second direction such that the aperture intersects both the first recess and the second recess. The implant insertion instrument further including a retention member configured to be slidably inserted into the aperture such that a first portion of the retention member is positioned in the first recess, a second portion of the retention member is positioned in the second recess, and a third portion of the retention member is positioned between the first recess and the second recess.

According to an aspect of the disclosure, an implant includes an implant body extending from a proximal end of the implant to a distal end of the implant, the implant body including an inner surface and an outer surface, the outer surface opposite the inner surface, the implant body being flexible such that the implant is configured to transition from a first configuration in which the inner surface is substantially planar to a second configuration in which the inner surface is substantially helical, the implant body including a plurality of projections that each extend from the outer surface, each of the plurality of projections defining a through hole.

According to an aspect of the disclosure a method of implanting a cuff onto a biological structure includes the steps of positioning an implant insertion instrument adjacent the biological structure such that a retention member of the implant insertion is between the cuff and the biological structure, moving the retention member relative to the cuff such that a surface of the cuff faces the biological structure, changing a shape of the surface of the cuff from planar to helical, wherein the helical shape defines at least one revolution about an axis, and securing the cuff to the biological structure such that the axis passes through the biological structure, and removal of the cuff from the biological structure in all directions perpendicular to the axis are blocked by interference of the surface and the biological structure.

BRIEF DESCRIPTION OF THE DRAWINGS

The foregoing summary, as well as the following detailed description of illustrative embodiments of the application, will be better understood when read in conjunction with the appended drawings. For the purposes of illustrating the present disclosure, there is shown in the drawings illustrative embodiments. It should be understood, however, that the application is not limited to the specific embodiments and methods disclosed, and reference is made to the claims for that purpose. In the drawings:

DETAILED DESCRIPTION OF ILLUSTRATIVE EMBODIMENTS

Figure 1:
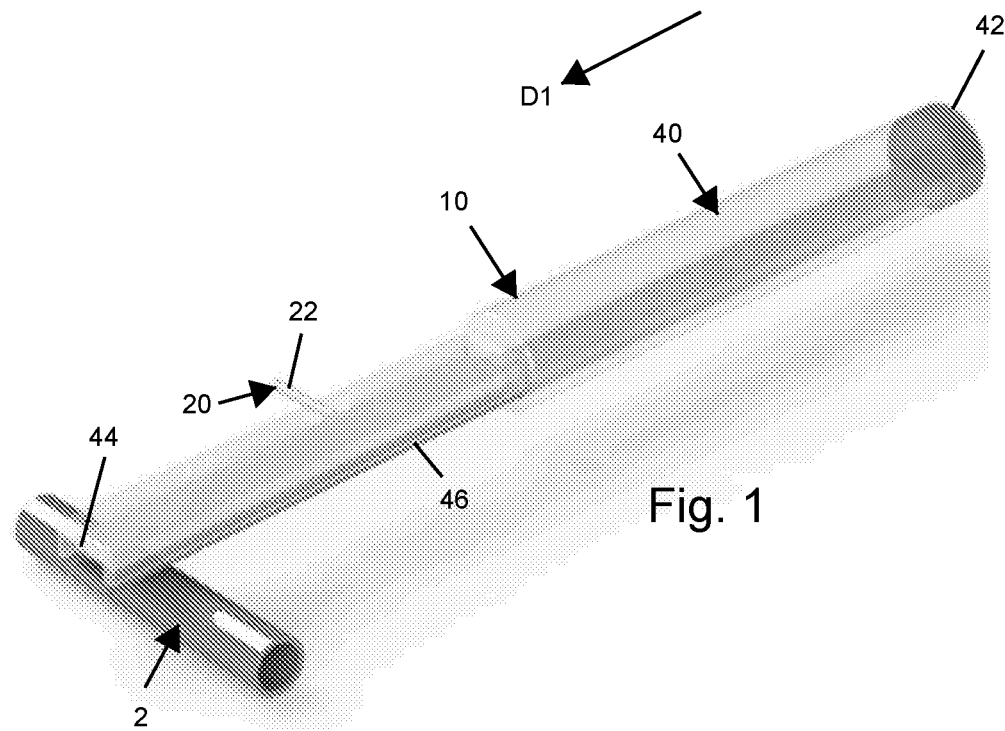
FIG. 1 is an isometric view of an implantable device and an insertion instrument configured to implant the implantable device, according to one aspect of the disclosure.

Certain terminology is used in the following description for convenience only and is not limiting. The term "aligned" as used herein in reference to two elements along a direction means a straight line that passes through one of the elements and that is parallel to the direction will also pass through the other of the two elements. The term "between" as used herein in reference to a first element being between a second element and a third element with respect to a direction means that the first element is closer to the second element as measured along the direction than the third element is to the second element as measured along the direction. The term "between" includes, but does not require that the first, second, and third elements be aligned along the direction.

Aspects of the disclosure will now be described in detail with reference to the drawings, wherein like reference numbers refer to like elements throughout, unless specified otherwise. Certain terminology is used in the following description for convenience only and is not limiting. The term "plurality," as used herein, means more than one. The terms "a portion" and "at least a portion" of a structure include the entirety of the structure. Certain features of the disclosure, which are described herein in the context of separate embodiments, may also be provided in combination in a single embodiment. Conversely, various features of the disclosure that are described in the context of a single embodiment may also be provided separately or in any subcombination.

Referring to FIGS. 1 to 11, an implantation system 10 can include an implant 20, an insertion instrument 40 (hereinafter the instrument 40), or both. The implant 20 can be a cuff 22 configured to be secured to a biological structure 2. The biological structure 2 can include, but is not limited to, soft tissue such as a blood vessel, or a nerve. The instrument 40 can be configured to advance the implant 20 to a location adjacent to the biological structure 2, and can further be configured to assist in securing the implant 20 to the biological structure 2.

The instrument 40 can include a proximal end 42, a distal end 44 spaced from the proximal end 42 in a first direction D1, and a body member 46 that extends from the proximal end 42 to the distal end 44 in the first direction D1, such that the body member 46 terminates at the proximal end 42 and the distal end 44 with respect to the first direction D1.

The body member 46 can include a distal surface 48 and a proximal surface 50. As shown in the illustrated embodiment, the distal surface 48 can be spaced from the proximal surface 50 in the first direction D1 such that the distal surface 48 faces the proximal surface 50. The body member can include a first side surface 52 and a second side surface 54, and the first side surface 52 can be spaced from the second side surface 54 in a second direction D2, which can be perpendicular to the first direction D1 as shown, such that the first side surface 52 faces the second side surface 54. The body member can include a base surface 56 that extends between the distal surface 48 and the proximal surface 50 in the first direction D1, and further extends between the first side surface 52 and the second side surface 54 in the second direction D2.

The first side surface 52 can include a first portion 53 and a second portion 55. The first portion 53 can be spaced from the second portion 55 in the first direction D1 such that a gap 59 is defined between the first portion 53 and the second portion 55 with respect to the first direction D1.

The instrument 40 can include a pocket 58 defined by the body member 46. As shown in the illustrated embodiment the pocket 58 can extend from the proximal surface 50 to the distal surface 48 in the first direction D1, can further extend from the second side surface 54 to the first side surface 52 in the second direction D2, and can further extend into the body member 46 in a third direction D3, which can be perpendicular to both the first direction D1 and the second direction D2 as shown, to the base surface 56.

The body member 46 can include a distal portion 49, at which the body member 46 terminates in the first direction D1. The distal portion 49 can include the distal surface 48, and the distal portion 49 can include a leading surface 51 opposite the distal surface 48, the leading surface 51 being tapered in the first direction D1. The leading surface 51 can be configured to separate the biological structure 2 from surrounding structures to assist in deployment of the implant 20.

Figure 3:
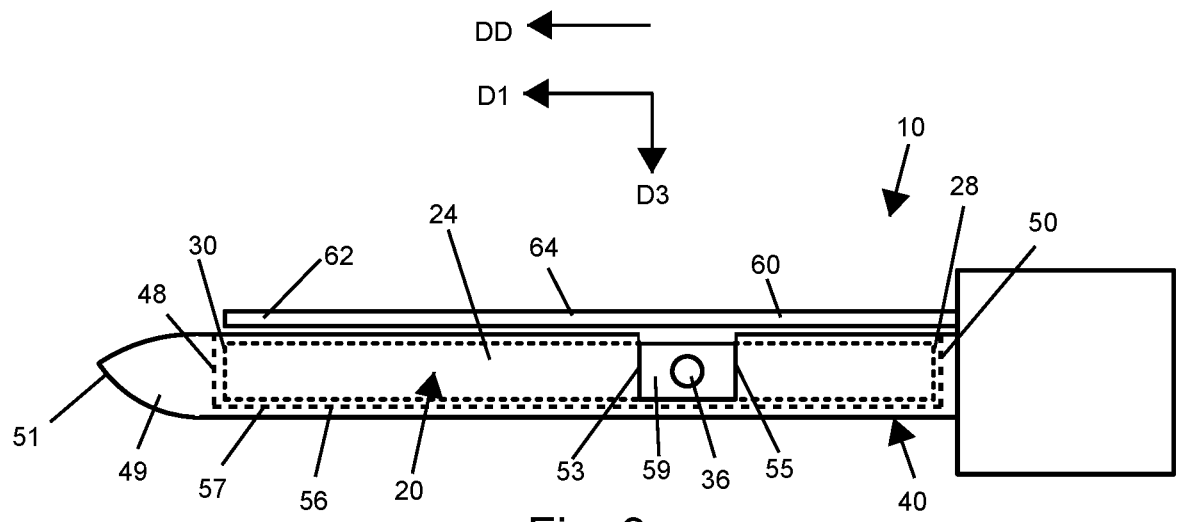
FIG. 3 is a side elevation view of the implantable device and an insertion instrument illustrated in FIG. 1, with a retention member of the insertion instrument in a first position.
Figure 4:
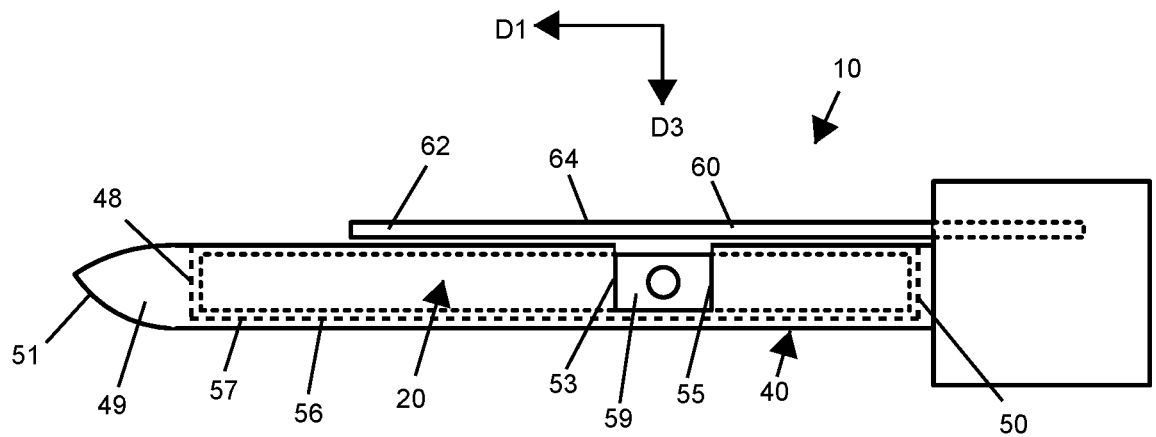
FIG. 4 is a side elevation view of the implantable device and an insertion instrument illustrated in FIG. 1, with the retention member of the insertion instrument in a second position.

The instrument 40 can include a retention member 60 configured to be movably attached to body member 46 such that the retention member 60 is movable from a first position relative to body member 46 to a second position relative to the body member 46. In the first position, for example as shown in FIG. 3, a portion 62 of the retention member 60 can be aligned with a portion 57 of the base surface 56 in the third direction D3, and in the second position, for example as shown in FIG. 4, the portion 62 of the retention member 60 is offset from the portion 57 of the base surface 56 in the third direction D3.

The pocket 58 can defines a length, a width, and a height. According to one aspect of the disclosure, the length can be measured from the proximal surface 50 to the distal surface 48 along the first direction D1, the width can be measured from the second side surface 54 to the first side surface 52 along the second direction D2, and the height can be measured from the portion 57 of the base surface 56 to the portion 62 of the retention member 60 along the third direction D3 when the retention member 60 is in the first position. As shown in the illustrated embodiment, the length can be is greater than the width, and the width can be greater than the height.

Referring to FIGS. 1 to 6, the retention member 60 can include a beam member 64. The beam member 64 can define a shape that corresponds to a shape of the pocket 58 such that when the retention member 60 is in the first position, at least a portion of the pocket 58 is covered by the retention member 60 such that the implant 20 positioned in the pocket 58 is prevented from exiting the pocket 58.

Figure 2:
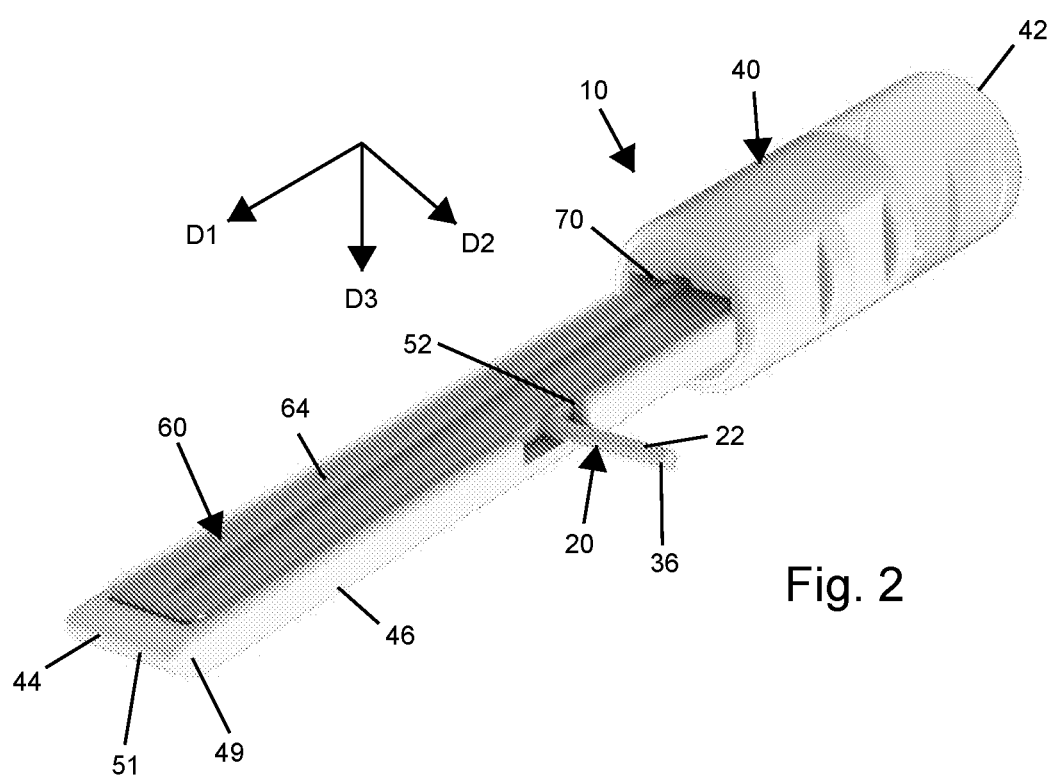
FIG. 2 is another isometric view of the implantable device and an insertion instrument illustrated in FIG. 1.
Figure 5:
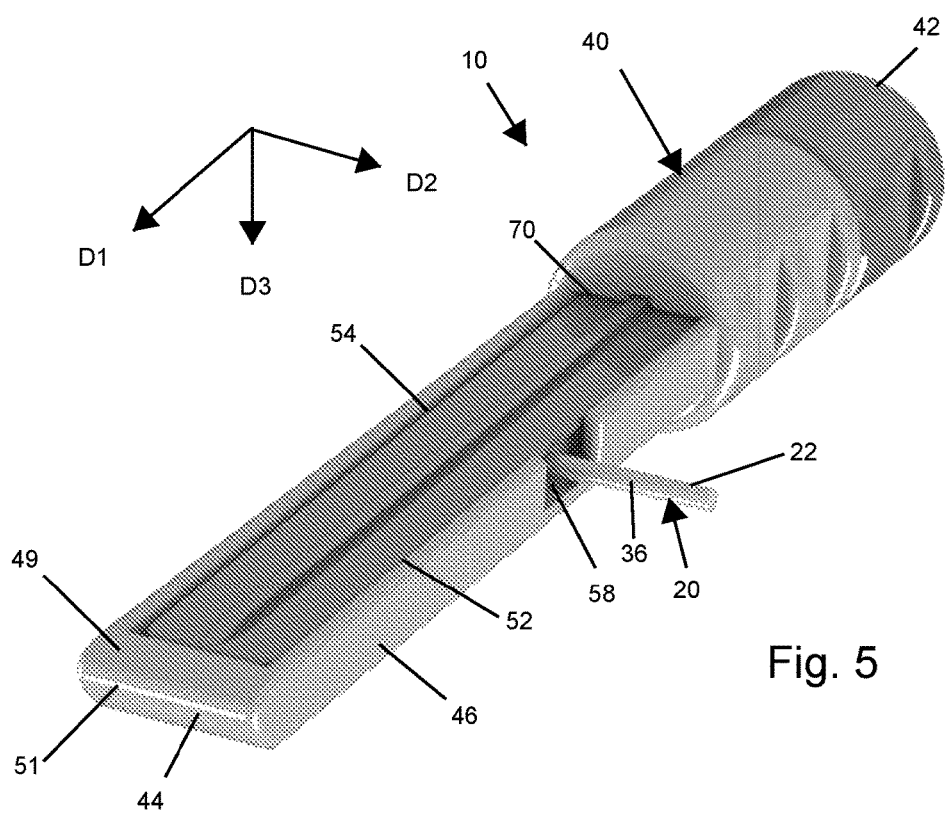
FIG. 5 is an isometric view of an implantable device and an insertion instrument configured to implant the implantable device, according to another aspect of the disclosure.
Figure 6:
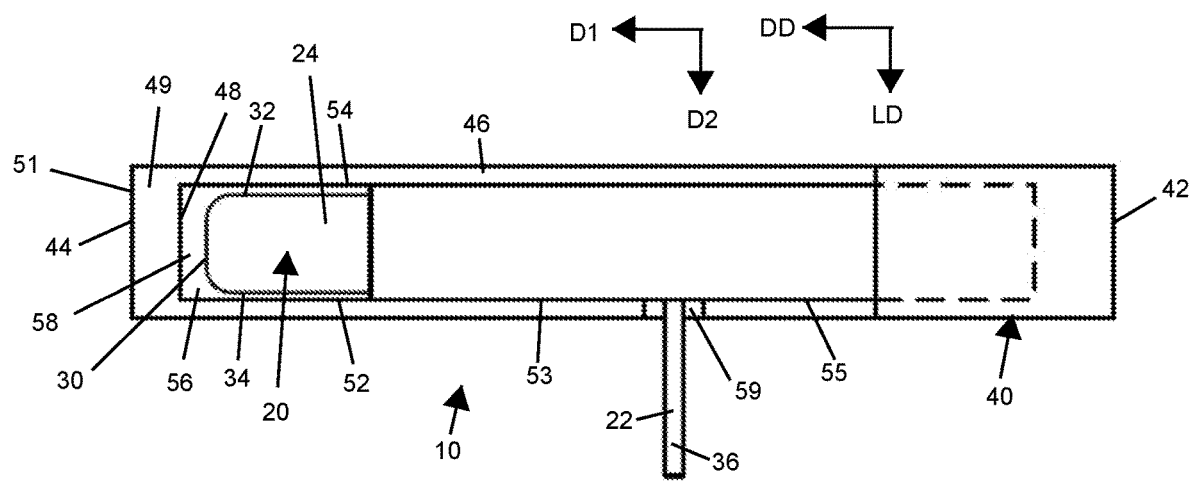
FIG. 6 is a top plan view of the implantable device and the insertion instrument illustrated in FIG. 5.

As shown in FIG. 2, the beam member 64 can define a width larger than the width of the pocket 58. As shown in FIG. 5, the beam member 64 can define a width smaller than the width of the pocket 58 such that the beam member 64 is configured to be attached to the body member in the first position, and in the first position the retention member 60 is aligned with both the first side surface 52 and the second side surface 54 in the second direction D2.

The body member 46 can define an opening 70 configured to slidably receive the retention member 60, such that the retention member 60 is configured to slide through the opening 70 in a direction opposite the first direction D1 to transition from the first position to the second position.

Figure 7:
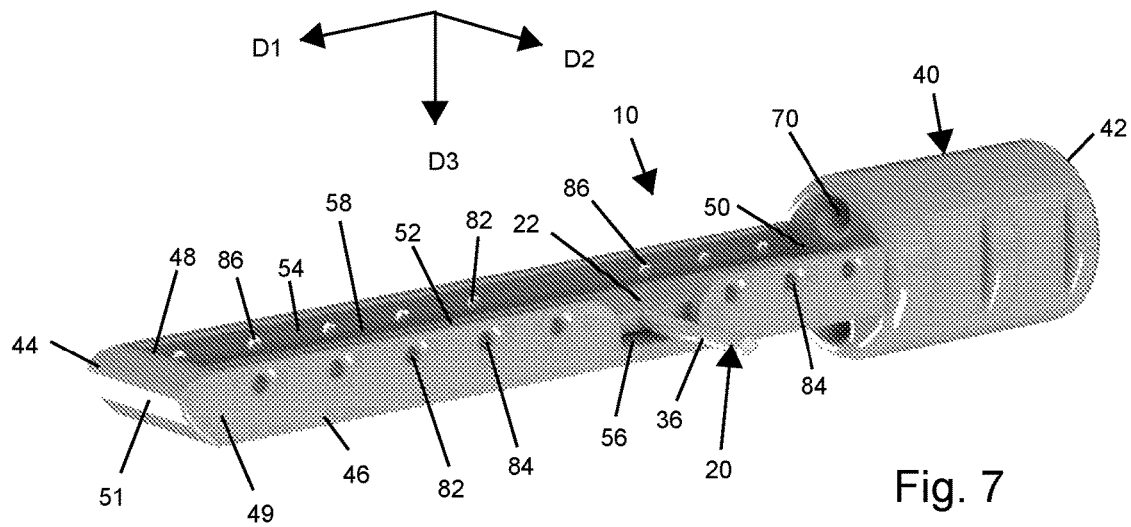
FIG. 7 is an isometric view of an implantable device and an insertion instrument configured to implant the implantable device, according to another aspect of the disclosure.
Figure 8:
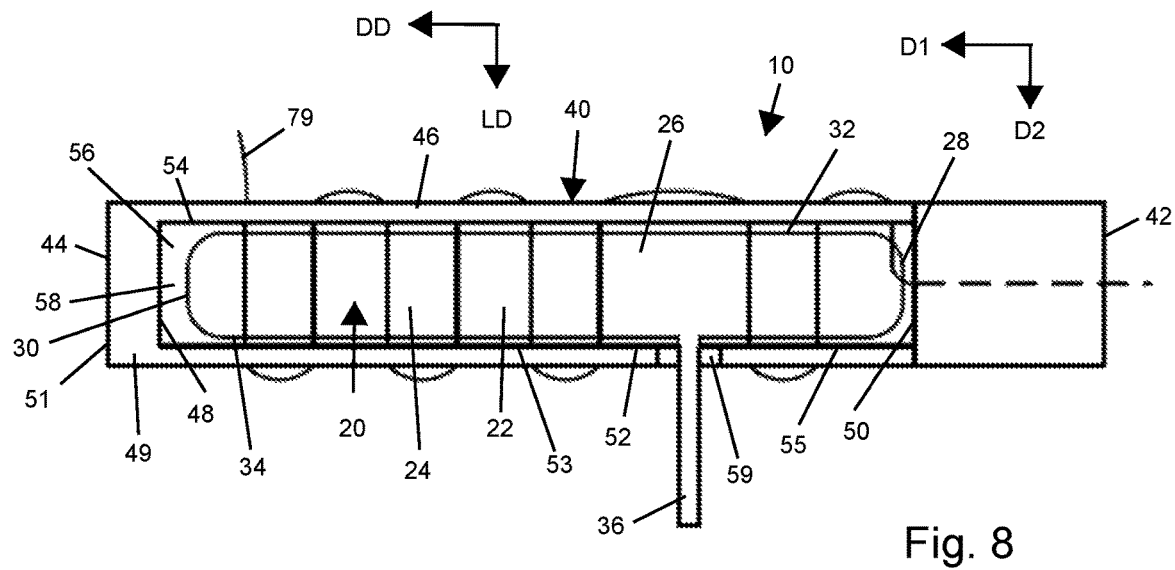
FIG. 8 is a top plan view of the implantable device and the insertion instrument illustrated in FIG. 7.
Figure 9:
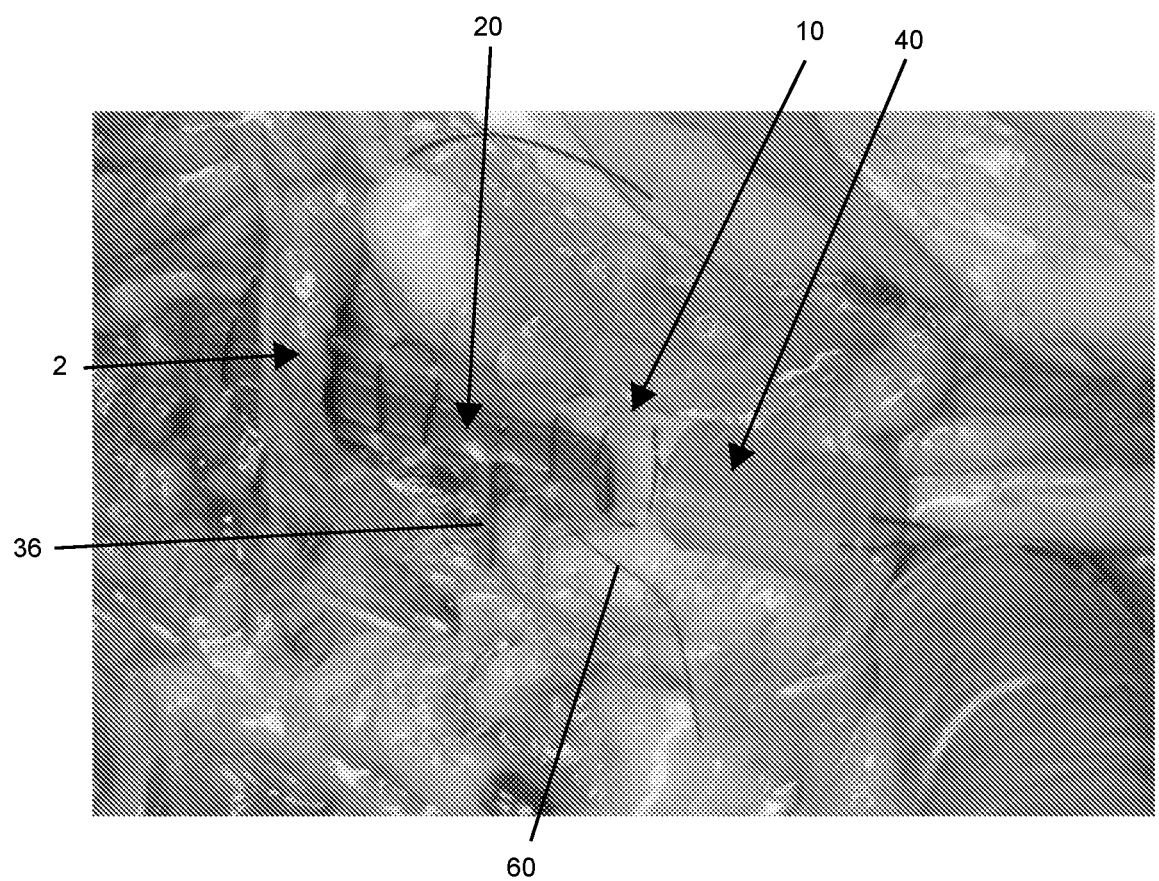
FIG. 9 is an isometric view of the implantable device and the insertion instrument illustrated in FIG. 7 during a procedure to secure the implantable device to a biological structure.

Referring to FIGS. 7 to 9, the retention member 60 can be flexible. According to one aspect of the disclosure the retention member 60 can be a monofilament, or multifilament element, such as a suture 79. The body member 46 can define a plurality of through holes 82 configured to receive the retention member 60. As shown in the illustrated embodiment, the plurality of through holes 82 can be defined by at least one of the first side surface 52 and the second side surface 54.

The plurality of through holes 82 can include a first series of through holes 84 and a second series of through holes 86. As shown, the first series of through holes 84 can be defined by the first side surface 52, and the second series of through holes 86 can be defined by the second side surface 54. The first series of through holes 84 can be aligned with the second series of through holes 86 in the second direction D2, as shown in the illustrated embodiment. According to another aspect of the disclosure, one or more of the first series of through holes 84 can be offset with respect to the second series of through holes 86.

The body member 46 can define the opening 70 configured to slidably receive the retention member 60, such that the retention member 60 is configured to slide through the opening 70 in a direction opposite the first direction D1 to transition from the first position to the second position.

The implantation system 10 can include a kit that includes the implant 20 coupled to the instrument 40, for example such that the implantable device is positioned within the pocket 58. The kit can include the implant 20 separate from the instrument 40.

Figure 10A:
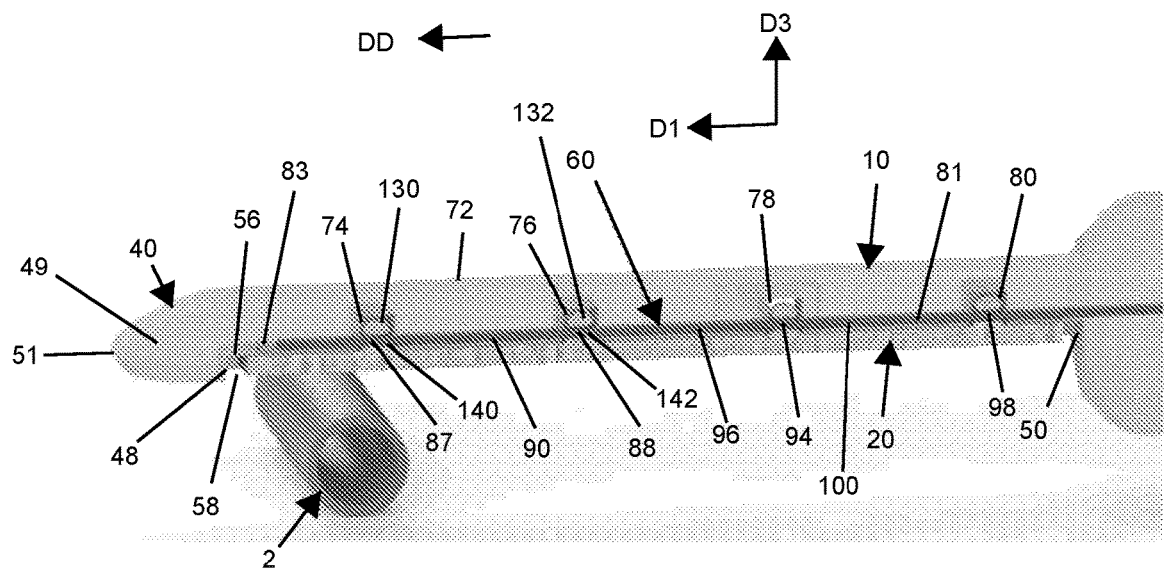
FIG. 10A is a cross-sectional view of an implantable device and an insertion instrument configured to implant the implantable device, according to another aspect of the disclosure.
Figure 10B:
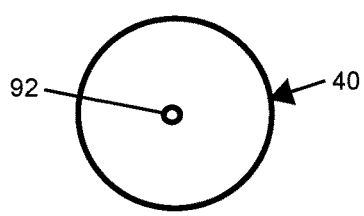
FIG. 10B is a rear elevation view of the insertion instrument illustrated in FIG. 10A.
Figure 11:
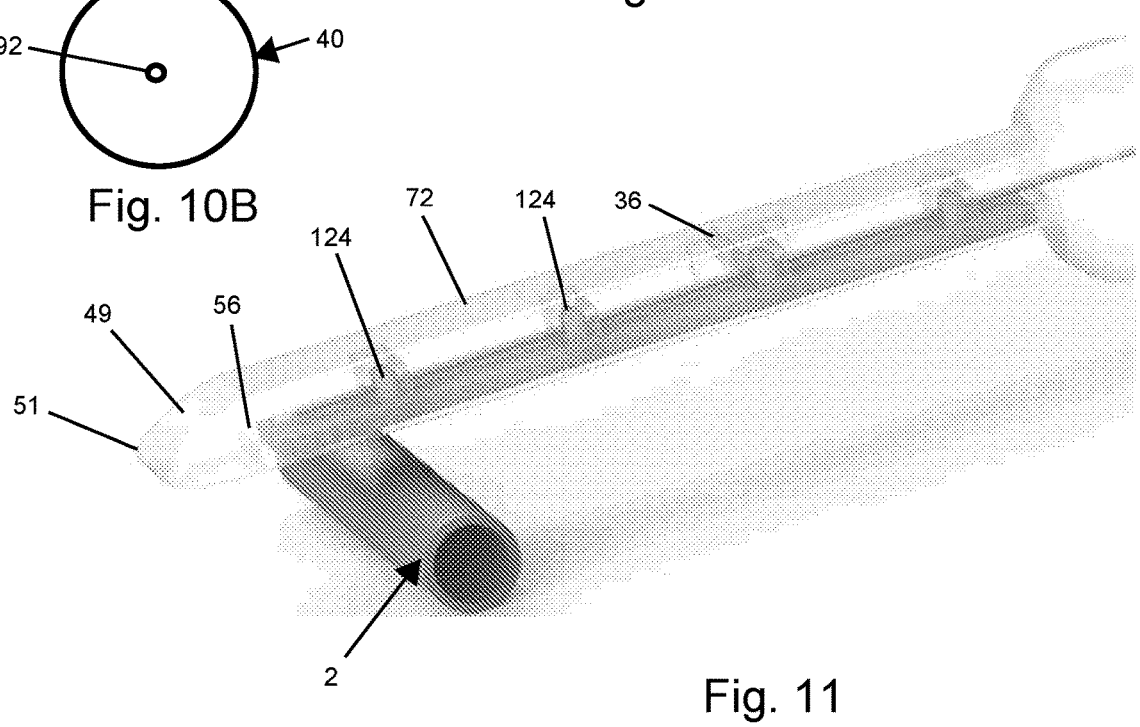
FIG. 11 is an isometric view of the implantable device and the insertion instrument illustrated in FIG. 10.
Figure 12:
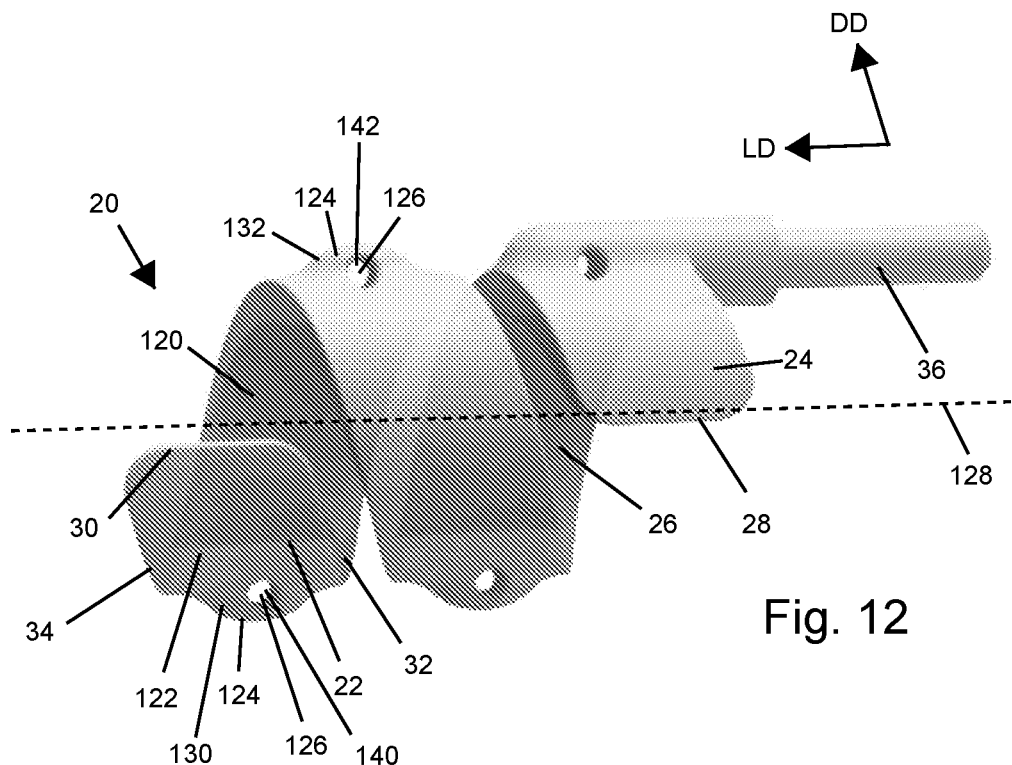
FIG. 12 is an isometric view of the implantable device illustrated in FIG. 10, in a deployed configuration.

Referring to FIGS. 10 to 12, the body member 46 can include an outer surface 72 that is opposite the base surface 56 with respect to the third direction D3. The instrument 40 can include a first recess 74 defined by the body member 46. As shown, the first recess 74 can extend into the base surface 56 toward the outer surface 72 and terminate between the base surface 56 and the outer surface 72 with respect to the third direction D3. The instrument 40 can include a second recess 76 defined by the body member 46 such that the second recess 76 extends into the base surface 56 toward the outer surface 72 and terminates between the base surface 56 and the outer surface 72 with respect to the third direction D3. As shown, the first recess 74 can be spaced from the second recess 76 in the first direction D1. The instrument 40 can include additional recesses, for example, a third recess 78 and a fourth recess 80, similar to the first recess 74 and the second recess 76.

The instrument 40 can include an aperture 83 defined by the body member 46, such that the aperture 83 extends in the first direction D1 and intersects one or more of the first recess 74, the second recess 76, the third recess 78, and the fourth recess 80. The retention member 60 can be a rod member 81 configured to be slidably inserted into the aperture 83 such that a first portion 87 of the retention member 60 is positioned in the first recess 74, a second portion 88 of the retention member 60 is positioned in the second recess 76, and a third portion 90 of the retention member 60 is positioned between the first recess 74 and the second recess 76.

The retention member 60 can be configured to be slidably inserted into the aperture 83 such that a fourth portion 94 of the retention member 60 is positioned in the third recess 78, and a fifth portion 96 of the retention member 60 is positioned between the second recess 76 and the third recess 78 in the first direction D1. The retention member 60 can be configured to be slidably inserted into the aperture 83 such that a sixth portion 98 of the retention member 60 is positioned in the fourth recess 80, and a seventh portion 100 of the retention member 60 is positioned between the third recess 78 and the fourth recess 80 in the first direction D1.

As shown, the retention member 60 can be configured to be slidably inserted into the aperture 83 such that the third portion 90 of the retention member 60 is positioned between the first recess 74 and the second recess 76 in the first direction D1, and the third portion 90 of the retention member 60 is positioned between the base surface 56 and the outer surface 72 in the third direction D3. The body member 46 can define an opening 92 of the aperture 83 such that the opening 92 faces in a direction opposite the first direction D1. The retention member can be configured to be slidably inserted through the opening 92 in the first direction D1 until the first portion 87 of the retention member 60 is positioned in the first recess 74.

Referring to FIGS. 1 to 14, the implant 20 can have a flexible body 24 such that the implant 20 is configured to transition between a first configuration and a second configuration. In the first configuration the implant 20 can define a first shape that corresponds to the pocket 58, such that at least a portion of the flexible body 24 is securable within the pocket 58. The flexible body 24 can include a first surface 26. In the first configuration the first surface 26 can be substantially planar (as shown in FIG. 3), and in the second configuration the first surface 26 can be substantially helical (as shown in FIG. 12). According to one aspect of the disclosure, the implant 20 can be configured such that the flexible body 24 is biased to the second configuration.

The flexible body 24 can extend from a proximal end 28 of the implant 20 to a distal end 30 of the implant 20. The implant 20 can be configured such that in the first configuration the distal end 30 is spaced from the proximal end 28 along a distal direction DD. The flexible body 24 can further extend from a first sidewall 32 to a second sidewall 34 in a lateral direction LD. The flexible body 24 can include a projection 36 that extends from one of the first sidewall 32 and the second sidewall 34. As shown, the projection 36 can extend from the second sidewall 34, and the system 10 can be configured such that the implant 20 can be inserted into the pocket 58 such that an entirety of the first surface 26 is positioned within the pocket 58, and the projection 36 extends through the gap 59 and is positioned outside the pocket 58.

Figure 13:
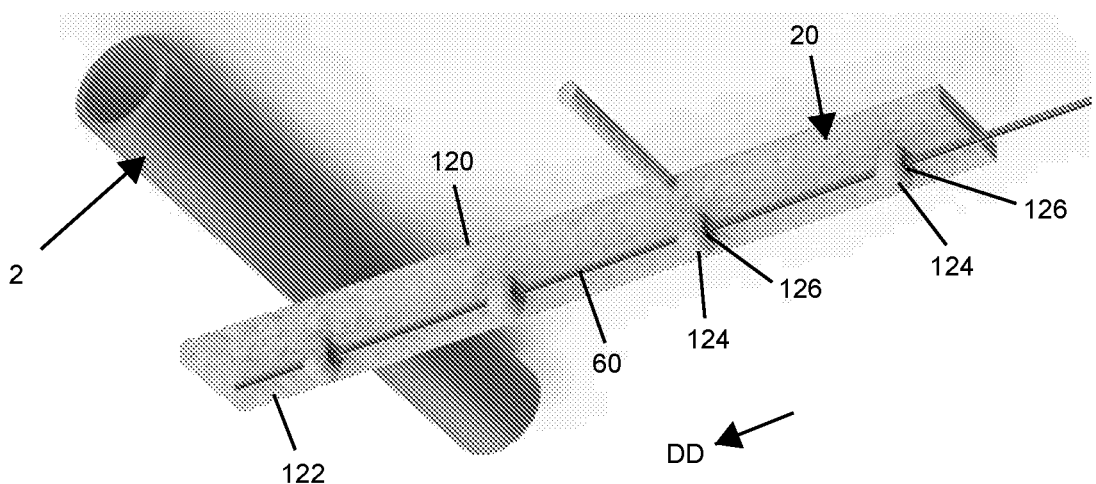
FIG. 13 is an isometric view of an implantable device according to another aspect of the disclosure.
Figure 14:
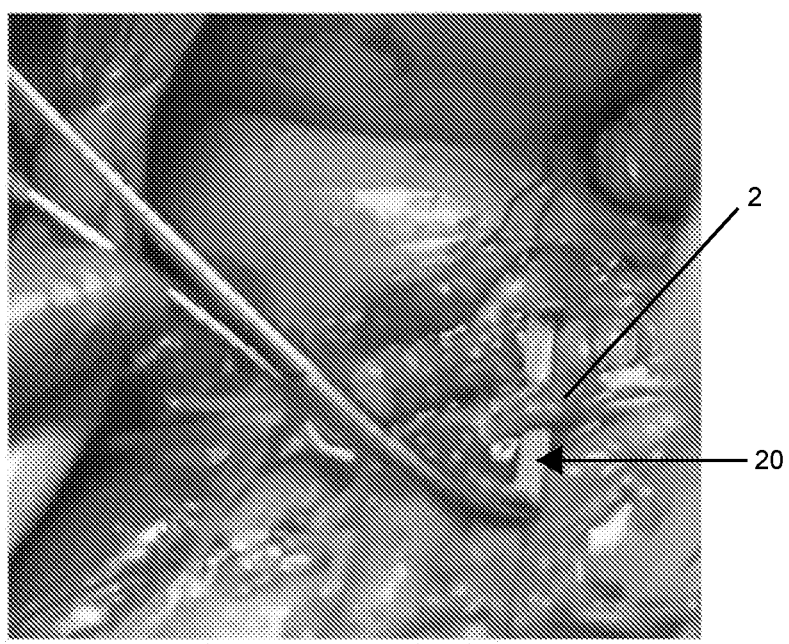
FIG. 14 is an isometric view of the implantable device illustrated in FIG. 13 during a procedure to secure the implantable device to a biological structure.
Figure 15:
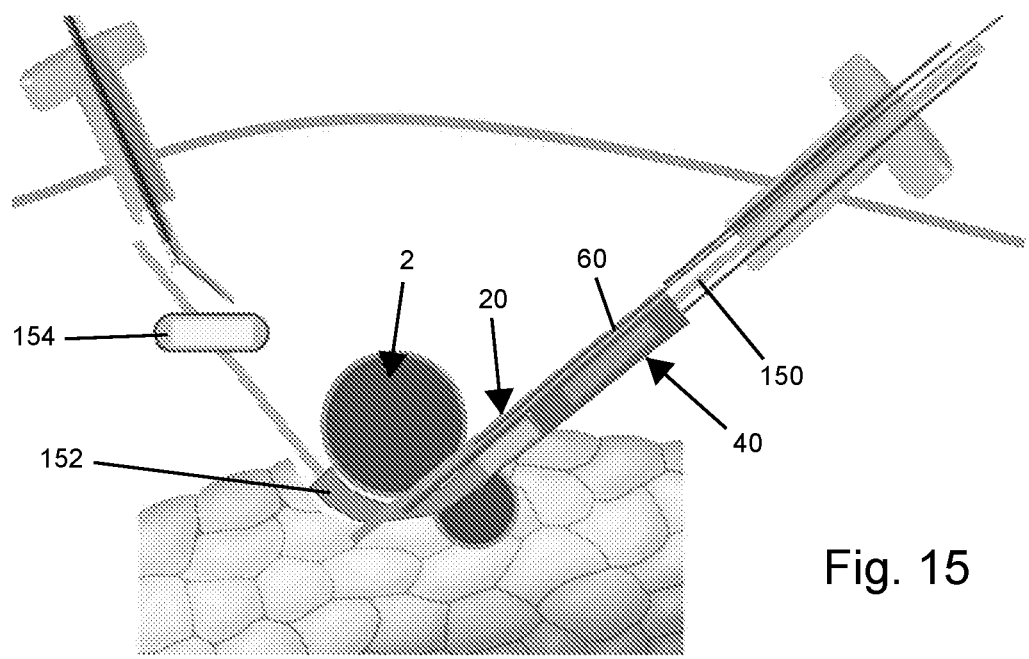
FIG. 15 is a schematic view of a step of a method of securing an implantable device to a biological structure.
Figure 16:
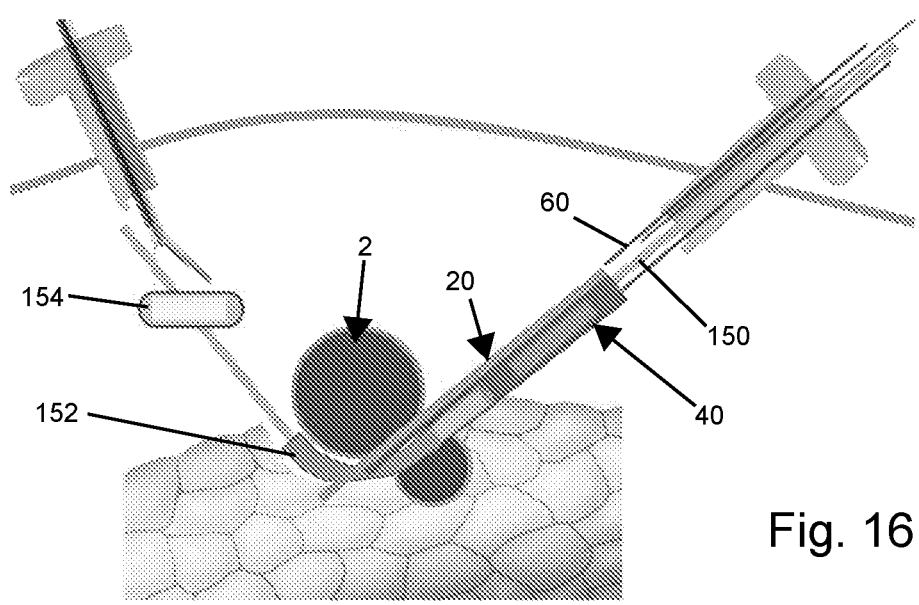
FIG. 16 is a schematic view of another step of the method illustrated in FIG. 15.
Figure 17:
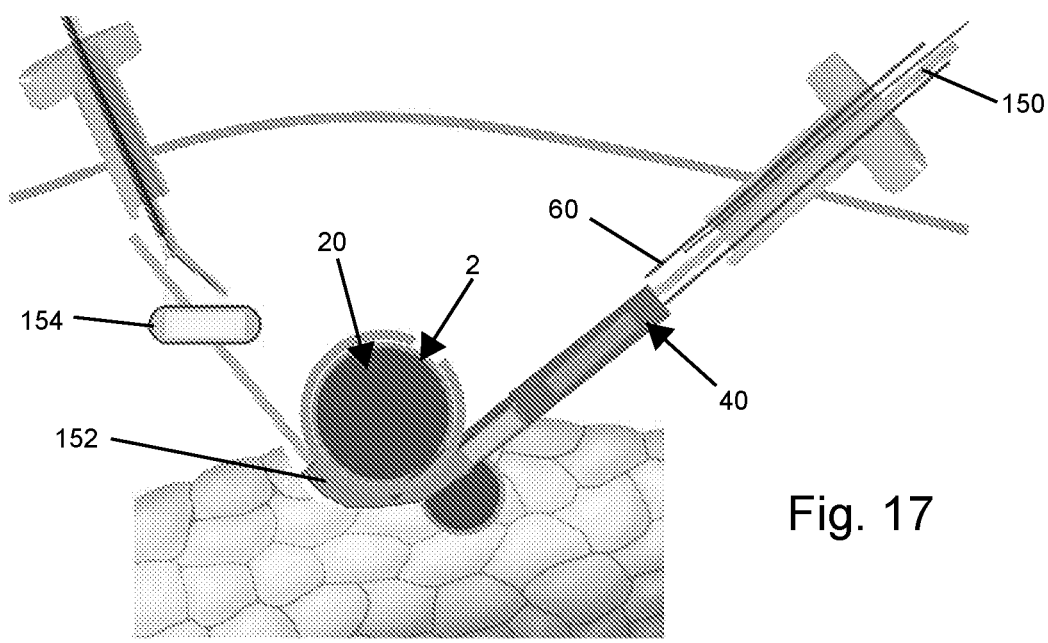
FIG. 17 is a schematic view of another step of the method illustrated in FIG. 15.
Figure 18:
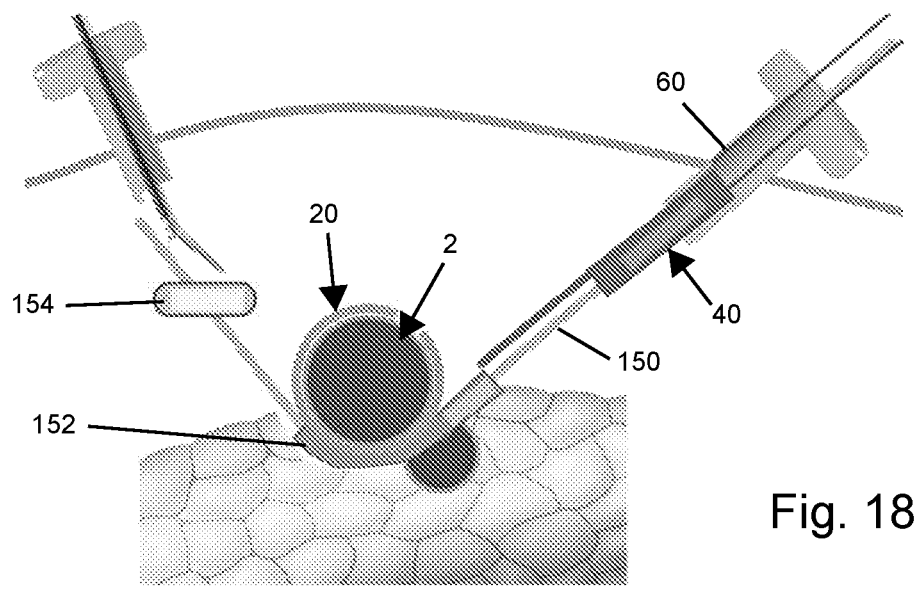
FIG. 18 is a schematic view of another step of the method illustrated in FIG. 15.

Referring to FIGS. 12 to 14, the flexible body 24 of the implant 20 can include an inner surface 120 and an outer surface 122. The inner surface 120 can include the first surface 26. The outer surface 122 can be opposite the inner surface 120, as shown in the illustrated embodiment. The flexible body 24 can be configured to transition from a first configuration in which the inner surface is substantially planar, for example as shown in FIG. 13, to a second configuration in which the inner surface is substantially helical, for example as shown in FIG. 12.

The implant 20 can include a plurality of projections 124 that each extend from the outer surface 122. As shown, the outer surface 122 can be substantially planar and the plurality of projections 124 each extend out from the outer surface 122 in a direction normal to the outer surface 122 at the location from which each of the plurality of projections 124 extends. Each of the plurality of projections 124 can define a respective through hole 126. The through holes 126 can be aligned along the distal direction DD.

The implant 20 can be configured such that in the second configuration the inner surface 120 is substantially helical about an axis 128, which is perpendicular to the distal direction DD. As shown, the axis 128 can be parallel to the lateral direction LD. According to one aspect of the disclosure, the implant 20 can be configured such that the projection 36 extends from the flexible body 24 in a direction that is parallel to the axis 128, for example the lateral direction LD.

The retention member 60 can be configured to be slidably inserted into the through hole 126 defined by each of the plurality of projections 124 when the implant is in the first configuration. The retention member 60 can be further configured to maintain the implant 20 in the first configuration. The implant 20 can be biased to the second configuration, such that removal of the retention member 60 from all of the through holes 126 results in transition of the implant 20 to the second configuration.

The system 10 can be configured such that the plurality of projections 124 includes a first projection 130 and a second projection 132, the first projection 130 spaced from the second projection 132 such that when the implant 20 is in the first configuration, the first projection 130 is configured to be inserted into the first recess 74, and the second projection 132 is configured to be inserted into the second recess 76, simultaneously.

The first projection 130 can define a first through hole 140, the second projection 132 can define a second through hole 142, and the instrument 40 can be configured to be coupled to the implant 20 such that the first projection 130 is positioned within the first recess 74, the second projection 132 is positioned within the second recess 76, the first through hole 140 is aligned with the aperture 83 in the first direction D1, and the second through hole 142 is aligned with the aperture 83 in the first direction D1. The retention member 60 can be configured to be slidably inserted into the aperture 83 such that a portion of the first portion 87 of the retention member 60 is positioned in the first through hole 140, and a portion of the second portion 88 of the retention member 60 is positioned in the second through hole 142, as shown in the illustrated embodiment.

As shown in FIG. 13, the system 10 can include the implant 20 and the retention member 60, and not include the instrument 40.

Referring to FIGS. 1 to 18, a method of implanting the implant 20 onto the biological structure 2 can include the step of positioning the instrument 40, which is coupled to the implant 20, adjacent the biological structure 2 such that the retention member 60 is between the implant 20 and the biological structure 2. The method can further include the step of coupling the implant 20 to the instrument 40. The coupling step can include the step of transitioning the implant 20 from the second configuration to the first configuration, and inserting the implant 20, while in the first configuration, into the pocket 58. The coupling step may further include the step of moving the retention member 60 to the first position such that the retention member 60 blocks movement of the implant 20 out of the pocket 58.

The positioning step may include the step of advancing the instrument 40 along a guide wire 150. The method can include the step of moving the retention member 60 relative to the implant 20 such that the inner surface 120 of the implant 20 faces the biological structure 2. The method can include the step of changing a shape of the inner surface 120 from planar to helical, and the helical shape defines at least one revolution about the axis 128. The method can include the step of securing the implant 20 to the biological structure 2 such that the axis 128 passes through the biological structure 2, and removal of the implant 20 from the biological structure 2 in all directions perpendicular to the axis 128 are blocked by interference of the inner surface 120 and the biological structure 2.

According to one aspect of the disclosure, the step of moving the retention member 60 includes the step of moving a portion of the retention member 60 through the plurality of holes 82 defined by the instrument 40. According to another aspect of the disclosure, the step of moving the retention member 60 includes the step of moving a portion of the retention member 60 through the plurality of holes 126 defined by the implant 20.

The method can further include the step of passing the implant 20 under biological structure 2. The step of passing the implant 20 can include the step of sliding the implant 20 along a ramp 152 configured to guide the implant 20 to a location of the biological structure 2. The method can further include the steps of removing the retention member 60 from the instrument 40, removing the instrument 40 from the position adjacent the biological structure 2, inflating a balloon 154, thereby increasing space available adjacent to the biological structure 2, or any combination thereof.

In an embodiment, an implant insertion instrument comprises a body member including a distal surface and a proximal surface, the distal surface spaced from the proximal surface in a first direction such that the distal surface faces the proximal surface, the body member further including a first side surface and a second side surface, the first side surface spaced from the second side surface in a second direction, which is perpendicular to the first direction, such that the first side surface faces the second side surface, the body member further including a base surface that extends between the distal surface and the proximal surface in the first direction, and further extends between the first side surface and the second side surface in the second direction; a pocket defined by the body member such that the pocket extends from the proximal surface to the distal surface in the first direction, further extends from the second side surface to the first side surface in the second direction, and further extends into the body member in a third direction, which is perpendicular to both the first direction and the second direction, to the base surface; and a retention member configured to be movably attached to body member such that the retention member is movable from a first position relative to body member to a second position relative to the body member, in the first position a portion of the retention member is aligned with a portion of the base surface in the third direction, and in the second position the portion of the retention member is offset from the portion of the base surface in the third direction.

In the embodiment of the implant insertion instrument, wherein the first side surface includes a first portion and a second portion, the first portion spaced from the second portion in the first direction such that a gap is defined between the first portion and the second portion with respect to the first direction.

In the embodiment of the implant insertion instrument, wherein the pocket defines a length, a width, and a height, the length measured from the proximal surface to the distal surface along the first direction, the width measured from the second side surface to the first side surface along the second direction, and the height measured from the portion of the base surface to the portion of the retention member along the third direction when the retention member is in the first position.

In the embodiment of the implant insertion instrument, wherein the length is greater than the width, and the width is greater than the height.

In the embodiment of the implant insertion instrument, wherein the retention member includes a beam member.

In the embodiment of the implant insertion instrument, wherein the body member defines an opening configured to slidably receive the beam member, such that the beam member is configured to slide through the opening in a direction opposite the first direction to transition from the first position to the second position.

In the embodiment of the implant insertion instrument, wherein the implant insertion instrument is configured such that when the retention member is attached to the body member and in the first position, the retention member is aligned with both the first side surface and the second side surface in the second direction.

In the embodiment of the implant insertion instrument, wherein the retention member is flexible.

In the embodiment of the implant insertion instrument, wherein the retention member is a suture.

In the embodiment of the implant insertion instrument, wherein the body member defines a plurality of through holes configured to receive the retention member.

In the embodiment of the implant insertion instrument, wherein the plurality of through holes are defined by at least one of the first side surface and the second side surface.

In the embodiment of the implant insertion instrument, wherein the plurality of through holes includes a first series of through holes and a second series of through holes.

In the embodiment of the implant insertion instrument, wherein the first series of through holes is defined by the first side surface, and the second series of through holes is defined by the second side surface.

In the embodiment of the implant insertion instrument, wherein the body member defines an opening configured to slidably receive the retention member, such that the retention member is configured to slide through the opening in a direction opposite the first direction to transition from the first position to the second position.

In the embodiment of the implant insertion instrument, wherein the body member includes a distal portion, the body member terminating at the distal portion in the first direction, the distal portion including the distal surface, the distal portion including a leading surface opposite the distal surface, the leading surface being tapered in the first direction.

In an embodiment a kit comprises the embodiment of the implant insertion instrument; an implant having a flexible body such that the implant is configured to transition between a first configuration and a second configuration, wherein in the first configuration the implant defines a first shape that corresponds to the pocket, such that at least a portion of the implant is securable within the pocket, and wherein in the second configuration the implant defines a second shape different than the first shape.

In the embodiment of the kit, wherein the implant includes a first surface, in the first configuration the first surface is substantially planar, in the second configuration the first surface is substantially helical.

In the embodiment of the kit, wherein the implant is biased to the second configuration.

In the embodiment of the kit, wherein the flexible body extends from a proximal end of the implant to a distal end of the implant, in the first configuration the distal end is spaced from the proximal end along a distal direction, the flexible further extends from a first sidewall to a second sidewall in a lateral direction, and the flexible body includes a projection that extends from the first sidewall.

In an embodiment, a second implant insertion instrument comprises a body member including a base surface and an outer surface, the outer surface opposite the base surface with respect to a first direction; a first recess defined by the body member, the first recess extending into the base surface toward the outer surface and terminating between the base surface and the outer surface with respect to the first direction; a second recess defined by the body member, the second recess extending into the base surface toward the outer surface and terminating between the base surface and the outer surface with respect to the first direction, the first recess spaced from the second recess in a second direction, which is perpendicular to the first direction; an aperture defined by the body member, the aperture extending in the second direction such that the aperture intersects both the first recess and the second recess; and a retention member configured to be slidably inserted into the aperture such that a first portion of the retention member is positioned in the first recess, a second portion of the retention member is positioned in the second recess, and a third portion of the retention member is positioned between the first recess and the second recess.

In the embodiment of the second implant insertion instrument, wherein the retention member is configured to be slidably inserted into the aperture such that the third portion of the retention member is positioned between the first recess and the second recess, and the third portion of the retention member is positioned between the base surface and the outer surface.

In the embodiment of the second implant insertion instrument, wherein the body member defines an opening of the aperture, and the opening faces in a direction opposite the second direction such that the retention member is configured to be slidably inserted through the opening in the second direction until the first portion of the retention member is positioned in the first recess.

In the embodiment of the second implant insertion instrument, further comprising a third recess defined by the body member, the third recess extending into the base surface toward the outer surface and terminating between the base surface and the outer surface with respect to the first direction such that the second recess is spaced from the third recess in the second direction, wherein the aperture intersects the third recess, and the retention member is configured to be slidably inserted into the aperture such that a fourth portion of the retention member is positioned in the third recess, and a fifth portion of the retention member is positioned between the second recess and the third recess.

In the embodiment of the second implant insertion instrument, further comprising a fourth recess defined by the body member, the fourth recess extending into the base surface toward the outer surface and terminating between the base surface and the outer surface with respect to the first direction such that the third recess is spaced from the fourth recess in the second direction, wherein the aperture intersects the fourth recess, and the retention member is configured to be slidably inserted into the aperture such that a sixth portion of the retention member is positioned in the fourth recess, and a seventh portion of the retention member is positioned between the third recess and the fourth recess.

In the embodiment of the second implant insertion instrument, wherein the body member includes a distal surface and a proximal surface, the distal surface spaced from the proximal surface in the second direction such that the distal surface faces the proximal surface, the body member further including a first side surface and a second side surface, the first side surface spaced from the second side surface in a third direction, which is perpendicular to both the first direction and the second direction, such that the first side surface faces the second side surface.

In the embodiment of the second implant insertion instrument, further comprising a pocket defined by the body member such that the pocket extends from the base surface in the first direction, further extends from the proximal surface to the distal surface in the second direction, and further extends from the second side surface to the first side surface in the third direction.

In the embodiment of the second implant insertion instrument, wherein the pocket defines a length, a width, and a height, the length measured from the proximal surface to the distal surface along the second direction, the width measured from the second side surface to the first side surface along the third direction, and the height measured from the base surface along the distal surface in the third direction.

In the embodiment of the second implant insertion instrument, wherein the length is greater than the width, and the width is greater than the height.

In an embodiment a second implant comprises an implant body extending from a proximal end of the implant to a distal end of the implant, the implant body including an inner surface and an outer surface, the outer surface opposite the inner surface, the implant body being flexible such that the implant is configured to transition from a first configuration in which the inner surface is substantially planar to a second configuration in which the inner surface is substantially helical, the implant body including a plurality of projections that each extend from the outer surface, each of the plurality of projections defining a through hole.

In the embodiment of the second implant, wherein in the first configuration the distal end is spaced from the proximal end in a distal direction.

In the embodiment of the second implant, wherein the through holes defined by each of the plurality of projections are aligned along the distal direction.

In the embodiment of the second implant, wherein in the second configuration the inner surface is substantially helical about a central axis, which is perpendicular to the distal direction.

In the embodiment of the second implant, further comprising a retention member configured to be slidably inserted into the through hole defined by each of the plurality of projections when the implant is in the first configuration, and the retention member is configured to maintain the implant in the first configuration.

In the embodiment of the second implant, wherein the implant is biased to the second configuration, such that removal of the retention member from all of the through holes defined by the plurality of projections results in transition of the implant to the second configuration.

In an embodiment a second kit comprises the embodiment of the second implant insertion instrument; and the embodiment of the second implant, wherein the plurality of projections includes a first projection and a second projection, the first projection spaced from the second projection such that when the implant is in the first configuration the first projection is configured to be inserted into the first recess, and the second projection is configured to be inserted into the second recess simultaneously.

In the embodiment of the second kit, wherein the first projection defines a first through hole, the second projection defines a second through hole, and the implant insertion instrument is configured to be coupled to the implant such that: 1) the first projection is positioned within the first recess, 2) the second projection is positioned within the second recess, 3) the first through hole is aligned with the aperture, and 4) the second through hole is aligned with the aperture.

In the embodiment of the second kit, wherein the retention member is configured to be slidably inserted into the aperture such that a portion of the first portion of the retention member is positioned in the first through hole, and a portion of the second portion of the retention member is positioned in the second through hole.

In an embodiment a method of implanting a cuff onto a biological structure, comprises the steps of positioning an implant insertion instrument adjacent the biological structure such that a retention member of the implant insertion is between the cuff and the biological structure; moving the retention member relative to the cuff such that a surface of the cuff faces the biological structure; changing a shape of the surface of the cuff from planar to helical, wherein the helical shape defines at least one revolution about an axis; and securing the cuff to the biological structure such that the axis passes through the biological structure, and removal of the cuff from the biological structure in all directions perpendicular to the axis are blocked by interference of the surface and the biological structure.

In the embodiment the method, wherein the step of moving the retention member includes the step of moving a portion of the retention member through a plurality of holes defined by the implant insertion instrument.

In the embodiment the method, wherein the step of moving the retention member includes the step of moving a portion of the retention member through a plurality of holes defined by the cuff.

It will be appreciated by those skilled in the art that changes could be made to the embodiments described above without departing from the broad inventive concept thereof. It is understood, therefore, that this disclosure is not limited to the particular embodiments disclosed, but it is intended to cover modifications within the spirit and scope of the present disclosure as defined by the claims.

What is claimed:

1. An implant insertion instrument comprising:
    a body member including a distal surface and a proximal surface, the distal surface spaced from the proximal surface in a first direction such that the distal surface faces the proximal surface, the body member further including a first side surface and a second side surface, the first side surface spaced from the second side surface in a second direction, which is perpendicular to the first direction, such that the first side surface faces the second side surface, the body member further including a base surface that extends between the distal surface and the proximal surface in the first direction, and further extends between the first side surface and the second side surface in the second direction;
    a pocket defined by the body member such that the pocket extends from the proximal surface to the distal surface in the first direction, further extends from the second side surface to the first side surface in the second direction, and further extends into the body member in a third direction, which is perpendicular to both the first direction and the second direction, to the base surface; and
    a retention member configured to be movably attached to the body member such that the retention member is slidably movable along a plane substantially opposite the first direction from a first position relative to the body member to a second position relative to the body member, in the first position a portion of the retention member is aligned with a portion of the base surface in the third direction, and in the second position the portion of the retention member is offset from the portion of the base surface in the first direction such that the base surface is accessible in the third direction.

2. The implant insertion instrument of claim 1, wherein the first side surface includes a first portion and a second portion, the first portion spaced from the second portion in the first direction such that a gap is defined between the first portion and the second portion with respect to the first direction.

3. The implant insertion instrument of claim 1, wherein the pocket defines a length, a width, and a height, the length measured from the proximal surface to the distal surface along the first direction, the width measured from the second side surface to the first side surface along the second direction, and the height measured from the portion of the base surface to the portion of the retention member along the third direction when the retention member is in the first position.

4. The implant insertion instrument of claim 3, wherein the length is greater than the width, and the width is greater than the height.

5. The implant insertion instrument of claim 1, wherein the retention member includes a beam member.

6. The implant insertion instrument of claim 5, wherein the body member defines an opening configured to slidably receive the beam member, such that the beam member is configured to slide through the opening in a direction opposite the first direction to transition from the first position to the second position.

7. The implant insertion instrument of claim 1, wherein the implant insertion instrument is configured such that when the retention member is attached to the body member and in the first position, the retention member is aligned with both the first side surface and the second side surface in the second direction.

8. The implant insertion instrument of claim 1, wherein the retention member is flexible.

9. The implant insertion instrument of claim 8, wherein the retention member is a suture.

10. The implant insertion instrument of claim 8, wherein the body member defines a plurality of through holes configured to receive the retention member.

11. The implant insertion instrument of claim 10, wherein the plurality of through holes are defined by at least one of the first side surface and the second side surface.

12. The implant insertion instrument of claim 11, wherein the plurality of through holes includes a first series of through holes and a second series of through holes.

13. The implant insertion instrument of claim 12, wherein the first series of through holes is defined by the first side surface, and the second series of through holes is defined by the second side surface.

14. The implant insertion instrument of claim 8, wherein the body member defines an opening configured to slidably receive the retention member, such that the retention member is configured to slide through the opening in a proximal direction along the first direction to transition from the first position to the second position.

15. The implant insertion instrument of claim 1, wherein the body member includes a distal portion, the body member terminating at the distal portion in the first direction, the distal portion including the distal surface, the distal portion including a leading surface opposite the distal surface, the leading surface being tapered in the first direction.

16. A kit comprising:
the implant insertion instrument of claim 1; and
an implant having a flexible body such that the implant is configured to transition between a first configuration and a second configuration,
wherein in the first configuration the implant defines a first shape that corresponds to the pocket, such that at least a portion of the implant is securable within the pocket, and
wherein in the second configuration the implant defines a second shape different than the first shape.

17. The kit of claim 16, wherein the implant includes a first surface, wherein in the first configuration the first surface is substantially planar, and wherein in the second configuration the first surface is substantially helical.

18. The kit of claim 16, wherein the implant is biased to the second configuration.

19. The kit of claim 16, wherein the flexible body extends from a proximal end of the implant to a distal end of the implant, and wherein in the first configuration the distal end is spaced from the proximal end along a distal direction, the flexible body further extends from a first sidewall to a second sidewall in a lateral direction, and the flexible body includes a projection that extends from the first sidewall.

* * * * *